United States Patent [19]

Gulbenk

[11] 4,025,333
[45] May 24, 1977

[54] SELECTIVELY HERBICIDAL 4,6-DIBROMO-5-HYDROXY-2-PYRIDINE CARBOXAMIDE, SALTS AND ESTERS THEREOF AND METHODS OF PREPARATION AND USE

[75] Inventor: Alin H. Gulbenk, Walnut Creek, Calif.

[73] Assignee: The Dow Chemical Company, Midland, Mich.

[22] Filed: Oct. 29, 1975

[21] Appl. No.: 626,679

Related U.S. Application Data

[63] Continuation-in-part of Ser. No. 541,812, Jan. 17, 1975, abandoned.

[52] U.S. Cl. .............................. 71/94; 260/247.2 A; 260/295 R; 260/247.2 B; 260/295 AM; 260/293.51; 260/240 R; 260/240 K
[51] Int. Cl.² ................. A01N 9/22; C07D 213/55; C07D 213/56
[58] Field of Search .... 260/247.2, 295 R, 295 AM, 260/293.51, 270 R, 240 R, 240 K; 71/94

[56] References Cited

UNITED STATES PATENTS

| | | | |
|---|---|---|---|
| 3,317,549 | 5/1967 | Johnston | 260/295 R |
| 3,761,486 | 9/1973 | McGregor | 260/295 AM |
| 3,862,952 | 1/1975 | Marley | 71/94 |
| 3,894,862 | 7/1975 | Whitaker et al. | 71/94 |
| 3,914,239 | 10/1975 | Kuhnis et al. | 260/295 R |

OTHER PUBLICATIONS

Heyns et al., Chemical Abstracts 49:10288–10289, (1955).
Undheim et al., Chemical Abstracts 71:30366g, (1969).

*Primary Examiner*—Norman A. Drezin
*Attorney, Agent, or Firm*—R. R. Stringham

[57] ABSTRACT

The invention is a genus of compounds of the formula

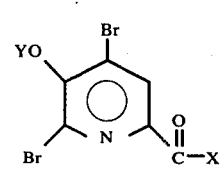

wherein X is —OH, —OM, —OR or —NH$_2$; Y is H, M or R'CO—; R is a primary or secondary C$_1$—C$_{12}$ alkyl group, a C$_5$—C$_7$ cycloalkyl group, phenyl or a C$_7$—C$_{12}$ phenalkyl or alylphenyl group; R' is a C$_1$—C$_{11}$ alkyl or alkenyl group, a C$_5$—C$_7$ cycloalkyl or cycloalkenyl group, phenyl or a C$_7$—C$_{12}$ phenyl alkyl, phenylalkenyl, alkylphenyl or alkenylphenyl group and M, independently, is a metal or ammonium cation. The compounds in which X is —NH$_2$ are uniquely selective post-emergent herbicides for control of both broadleaf weeds and wild oats in grains such as wheat and barley. The compounds in which X is not NH$_2$ have utility as intermediates and some of them are biologically active.

15 Claims, No Drawings

SELECTIVELY HERBICIDAL 4,6-DIBROMO-5-HYDROXY-2-PYRIDINE CARBOXAMIDE, SALTS AND ESTERS THEREOF AND METHODS OF PREPARATION AND USE

CROSS REFERENCE TO RELATED APPLICATIONS

This is a continuation-in-part of application Ser. No. 541,812, filed Jan. 17, 1975 abandoned.

BACKGROUND OF THE INVENTION

The chemicals presently used for weed control in wheat or barley either control wild oats or broadleaf weeds but none of them adequately control both broad-leaves and wild oats. For example, the commercial herbicide, BROMINIL®

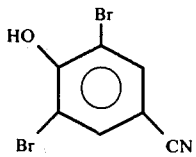

and 2,4-D control broadleaf weeds but not wild oats, whereas the commercial herbicide, CARBYNE®

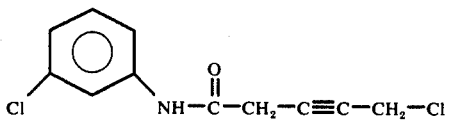

controls wild oats effectively but does not adequately control broadleaved plants.

5-Hydroxy-2-pyridine carboxylic acid and the methyl ester (of the carboxyl group) are known compounds, but no reference to the amide or to any brominated derivatives of any of these compounds has been found in the literature.

U.S. Pat. No. 3,651,070 discloses several specific compounds of the formula

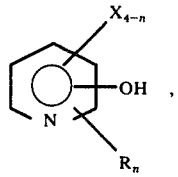

where X is halogen, n is 1 or 2 and R is like or unlike radicals of the carboxylate group, including acids, salts and esters thereof. The disclosed species are said to have utility as herbicides, bactericides and fungicides. Among these, the closest compound to those of the present invention is trichloro-4-hydroxypicolinic acid. No compounds in which X is other than chlorine or in which R is —CONH$_2$ are disclosed. The only pertinent activity data given is for applications of the above-named compound, as such and as the potassium salt, at a level of at least 64 lbs. per acre to tomatoes, beans, corn, and oats. Complete plant kill only of tomatoes is reported.

The compound 3,5-diiodo-4-hydroxybenzamide is reported (Cooke et al; Proc. Northeast Weed Control Conf., 19, 321-3 (1965)) to be inactive and 3,5-dibromo-4-hydroxybenzonitrile is shown to be less active than 3,5-diiodo-4-hydroxybenzonitrile.

SUMMARY OF THE INVENTION

Selective, post-emergent activity against both broad-leaf weeds and wild oats in grains such as wheat and barley is exhibited by certain new herbicidal compounds of the formula

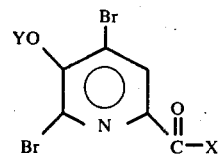

wherein X is —OH, —OM, —OR or —NH$_2$; Y is H, M or R'CO—; R is a primary or secondary C$_1$-C$_{12}$ alkyl group, a C$_5$-C$_7$ cycloalkyl group, phenyl or a C$_7$-C$_{12}$ phenylalkyl or alkylphenyl group; R' is a C$_1$-C$_{11}$ alkyl or alkenyl group, a C$_5$-C$_7$ cycloalkyl or cycloalkenyl group, phenyl or a C$_7$-C$_{12}$ phenalkyl, phenalkenyl, alkylphenyl or alkenylphenyl group and M, independently, is a metal or ammonium cation. In the preceding definition of M, the term "metal" means lithium sodium, potassium, calcium, magnesium, barium, aluminum, a metal of atomic number 24 through 30 or tin; the term "ammonium" means (H-NR''R$_2$''')$^+$, R'' being H, an alkyl or alkenyl group of 1 to 22 carbons, a hydroxyalkyl group of 2 to 4 carbons, a cycloalkyl group of 3 to 7 carbons, or benzyl; and the two R''' groups, together with the nitrogen, constitute a morpholine or piperidine ring or are independently defined as is R''.

The compounds of the above genus in which —X is —NH$_2$ are selective herbicides against both broadleaf weeds and wild oats in grains such as wheat and barley and constitute a preferred embodiment of the invention. Some of the compounds of the invention exhibit fungicidal, nematicidal, or insecticidal activity. All of the compounds are useful as chemical intermediates. For example, 4,6-dibromo-5-hydroxy-2-pyridine carboxylic acid has utility as a monomer for preparation of fire retardant polyesters and as a co-reactive curing agent (cross-linker) for epoxy resins, urethane prepolymers, etc.

The compounds of the invention are white or light colored, relatively high melting solids which, except in the case of the ammonium or metal salts, are moderately soluble in the common organic solvents and are of low solubility in water. The salts are generally soluble in water and insoluble in all but the most highly polar organic solvents.

Another aspect of the invention is considered to be the method of preparing 4,6-dibromo-5-hydroxy-2-pyridinecarboxamide which comprises reacting an ester of the formula

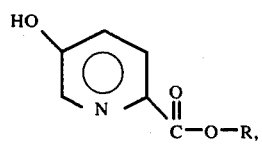

wherein R is defined as in the preceding generic formula, with bromine in the presence of water and then reacting the resultant 4,6-dibromo derivative with aqueous ammonia.

In a further aspect, the invention is a method of controlling plant growth comprising distributing in an area where the plants are grown, in an amount effective to control their growth, a compound as above defined.

DETAILED DESCRIPTION OF THE INVENTION

The most active herbicides among the compounds of the invention are those in which X, in the preceding formula, is $-NH_2$ and Y is H, "ammonium", sodium or R'CO-, wherein R' is a linear alkyl group of 1 to 11 carbons. By reason of cost, ease of formulation and selectivity for wheat and barley, the compounds within this group in which Y is H or R'CO and R' contains 1 to 7 carbons are preferred, R' = methyl being particularly preferred.

Within the sub-class of the present compounds in which Y is "ammonium", i.e., - $(HN-R''R_2''')^+$- the most active species are the 3-pyridinol salts of triethanolamine and N-methyl morpholine.

METHODS OF PREPARATION

Suitable precursor esters for the preparation of the new dibromo esters (and amides, thereafter) by the method of the present invention are those of the formula

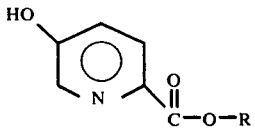

wherein R is as defined in the generic formula supra. Such esters may be prepared in two steps from 3-hydroxy pyridine (available from Aldrich Chemical Co.), by known procedures. Briefly, 3-hydroxy pyridine is first reacted with $CO_2$ under pressure in the presence of anhydrous potassium carbonate at an elevated temperature. The resulting 5-hydroxy-2-pyridine carboxylic acid is converted to an aliphatic or aromatic ester as above defined by reacting it with the corresponding hydroxy compounds in the presence of a strongly acid catalyst, such as a mineral acid for example.

The preparative method of the present invention comprises brominating the precursor ester in water and then reacting the resulting 4,6-dibromo derivative with aqueous ammonia (ammonium hydroxide), thereby converting the ester group to a carboxamide group. Within the preceding limitations, the choice of the R group is not critical to the success of these two reactions. However, those esters in which R is a primary or secondary alkyl group of 1 to 12 carbons are preferred intermediates by reason of the corresponding alkanols being readily available, liquid at room temperature and easily esterified.

Both reactions will proceed as two-phase reactions, i.e., as reactions of slurries or dispersions of the organic reactant in an aqueous solution of the inorganic reactant. Consequently, solubility of the starting ester is not an important consideration. Desirably, from the standpoint of economy, the "R" moiety does not itself consume bromine. However, all that is really essential is that the ester group is not hydrolyzed and decarboxylated during the bromination and is subsequently convertible to the carboxamide by reaction with aqueous ammonia.

When the precursor ester is to be prepared by reaction of 5-hydroxy-2-pyridine carboxylic acid with an alcohol in the presence of an acid catalyst, it is desirable that the alcohol employed be one which is liquid at moderate temperatures. Alcohols which are liquid at ordinary ambient temperatures are preferred. Methanol and ethanol are particularly suitable.

The preparative process of the present invention will now be described in greater detail.

BROMINATION

The precursor ester is contacted, as an aqueous dispersion or solution, with bromine. Preferably, the ester is first dispersed or dissolved in water and liquid bromine added slowly with stirring. However, the sequence or method of introduction of the reactants is not critical to obtaining at least a partial conversion of the ester to the desired 4,6-dibromo derivative.

The amount of water employed in the reaction mixture is not critical but should be sufficient to facilitate stirring. The mole ratio of bromine to the precursor ester is not critical to attaining at least partial conversion to the dibromo compound, since, the monobromo intermediate reacts more readily with bromine than the unbrominated ester and introduction of a third atom of bromine does not tend to occur under the conditions employed. However, ratios of from about 1.8/1 to about 2.2/1 are desirable. In the preferred mode of operation, wherein the bromine is added incrementally, the progress of the reaction may be judged by the rate at which the characteristic bromine color fades out. The reaction is essentially complete when the bromine color persists.

Desirable bromination temperatures are within the range of about 0° C. to about 40° C. Temperatures within the range of about 20°-30° are preferred as providing relatively rapid reaction rates with minimal side reaction.

The bromination product is readily recovered and purified by such conventional procedures as filtration, washing and recrystallization from a suitable solvent (benzene/hexane, for example).

Ester to Amide Conversion

The 4,6-dibromo-5-hydroxy-2-pyridinecarboxylic acid ester is intimately contacted with aqueous ammonia, desirably at a temperature of from about 35°-75° C. until the desired proportion of the ester has been converted to the amide. Neither the manner of introducing the reactants or of contacting them is critical. Conveniently, a slurry of the ester in concentrated aqueous ammonia is stirred, as by an impeller or a recirculating pump. Alternatively, ammonia may be introduced to a slurry of the ester in water or an aqueous ammonia solution passed through a bed of the finely particulated ester. The concentration of the aqueous ammonia (ammonium hydroxide) is not critical and ordinary commercial ($\sim$29% $NH_3$) ammonium hydroxide is generally highly suitable.

The amount of aqueous ammonia used should provide at least one molecular proportion of ammonia for each molecular proportion of the ester to be converted and should contain at least enough water to facilitate stirring or pumping.

The immediate product of the reaction is the salt formed by reaction of ammonia and the acidic -OH group in the desired amide (Y, in the generic structure supra, $= NH_4^+$). The amide is liberated from the salt by neutralization with a dilute acid, such as hydrochloric acid for example, and freed of any unconverted ester by extraction (leaching) with a suitable solvent, such as methanol/benzene.

4,6-Dibromo-5-hydroxy-2-pyridinecarboxylic acid may be prepared from a corresponding 2-ester by heating a mixture of the ester with an aqueous solution of a strong base, such as sodium hydroxide and then cooling and neutralizing with a dilute acid. Conveniently, the saponification reaction is carried out at the reflux temperature of the mixture.

Metal and ammonium salts of acidic 5-hydroxy group (and/or of the 2-carboxyl group when R is H) are prepared by conventional procedures for the preparation of such salts. The carboxylate esters of the 5-hydroxy group, wherein Y is an acyl group as above defined, are made by reacting a dibromo-5-hydroxy compound of the invention with the corresponding acyl chloride in pyridine. In a narrower aspect, the preparative method of the present invention comprises any of the foregoing several procedures as one or more additional steps.

PREPARATIVE EXAMPLES

EXAMPLE 1

5-Hydroxy-2-pyridinecarboxylic Acid Methyl Ester (Compound No. 1):

Gaseous hydrogen chloride was passed through a solution of 5 g of dry 5-hydroxy-2-pyridinecarboxylic acid in 100 ml methanol for 5 hours at 70° C. The mixture was kept for 2 days at room temperature and the solvent removed in vacuo. The residue was taken up in a minimum amount of water and neutralized with ammonium hydroxide. The precipitate was removed by filtration and the ester was separated in 70% yield from the acid by recrystallizing from isopropyl alcohol; m.p. 188°–190°.

Calc. for $C_7H_7NO_3$: C, 55.0; H, 4.6; N, 9.2. Found: C, 56.3; H, 5.3; N, 9.6.

EXAMPLE 2

4,6-Dibromo-5-hydroxy-2-pyridinecarboxylic acid, Methyl Ester (Compound No. 2):

To a stirred solution of 15 g 5-hydroxypyridine-2-carboxylic acid methyl ester in 300 ml water, 31.2 g bromine was added slowly. The mixture was stirred until disappearance of the bromine color resulted. Then the solid was removed by filtration, washed with cold water, and recrystallized from benzene/hexane (2:3, respectively) in 67% yield; m.p. 148°–150° C.

Calc. for $C_7H_5Br_2NO_3$: Br, 51.0. Found: Br, 51.2.

The structure of the product was confirmed by Nuclear Magnetic Resonance (NMR).

EXAMPLE 3

4,6-Dibromo-5-hydroxy-2-pyridinecarboxamide (Compound No. 3):

Concentrated ammonium hydroxide, 180 ml, was added to 10 g of 4,6-dibromo-5-hydroxy-2-pyridinecarboxylic acid methyl ester and heated at 45°–60° C. for 1 hour. After the mixture was kept for 2 days at room temperature, the solid was filtered and successively washed with dilute HCl (to neutralize the ammonia) and then with methanol and benzene to remove any unreacted starting material. The product was isolated in 80% yield; m.p. 261–266° C. (best sample: m.p. 275° C.).

Calc. for $C_6H_4Br_2N_2O_2$: C, 24.0; H, 1.3; N, 9.4. Found: C, 24.7; H, 1.5; N, 9.4.

EXAMPLE 4

4,6-Dibromo-5-hydroxy-2-pyridinecarboxylic acid (Compound No. 4):

A solution of 0.5 g sodium hydroxide in 15 ml of water was added to 2 g of 4,6-dibromo-5-hydroxy-2-pyridine-carboxylic acid methyl ester and refluxed for 2 hours. The product was isolated, by cooling and acidifying with concentrated hydrochloric acid, in 53% yield; m.p. 195°–197° C.

Calc. for $C_6H_3Br_2NO_3$: C, 24.3; H, 1.0; N, 4.7; Br, 53.6. Found: C, 24.4; H, 1.1; N, 4.6; Br, 53.74.

EXAMPLE 5

2,4-Dibromo-3-octanoyl-oxy-6-pyridinecarboxamide (Compound No. 5):

To a solution of 3 g of 4,6-dibromo-5-hydroxy-2-pyridinecarboxamide in 15 ml pyridine, 1.6 g of octanoyl chloride was added slowly at room temperature. The mixture was allowed to stir for 3-4 hours. The product, mp 136°–8°, was isolated in 92% yield by quenching the reaction mixture over ice, removing the solid by filtration and recrystallizing from benzene.

Calc. for $C_{14}H_{18}Br_2N_2O_3$: C, 39.8; H, 4.33; Br, 37.9; N, 6.6; O, 11.4. Found: C, 39.9; H, 4.2; Br, 37.5; N, 6.6

In essentially the same manner, the following 3-alkanoyloxy compounds (esters) were prepared, care being taken to avoid hydrolysis of the products:

| Compound No. | Alkanoyl Group | m.p. ° C. | % Theoretical Yield |
|---|---|---|---|
| 6 | $CH_3CO-$ | 201–2 | 63 |
| 7 | $CH_3-CH_2CO-$ | 192.5–193.5 | 58.5 |
| 8 | $CH_3(CH_2)_2CO-$ | 169–170 | 58.1 |
| 9 | $CH_3(CH_2)_4CO-$ | 145–146 | 64.0 |
| 10 | $CH_3(CH_2)_3CH(C_2H_5)CO-$ | 129.–130.5 | 83.6 |
| 11 | $CH_3(CH_2)_8CO-$ | 129–130 | 67.0 |
| 12 | $OCO-$ | 226–228 | 70.0 |
| 13 | $(CH_3)_2CH-CO-$ | 161–163 | 81.0 |

EXAMPLE 6

The following esters of the invention are made by reacting 5-hydroxy-2-pyridinecarboxylic acid with the corresponding known hydroxy compound, R-OH, in the presence of an acid catalyst, such as sulfuric acid or hydrogen chloride — as per Example 1 herein — and contacting the resulting esters with water and bromine, as per Example 2 herein:

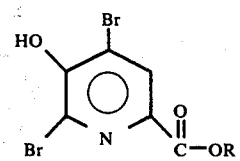

| Compound No. | R |
|---|---|
| 14 | Phenyl |
| 15 | Ethyl |
| 16 | Isopropyl |
| 17 | Isobutyl |
| 18 | n-Hexyl |
| 19 | 2-Octyl |
| 20 | 1-Dodecyl |

-continued

| Compound No. | R |
|---|---|
| 21 | Cyclopentyl |
| 22 | Cycloheptyl |
| 23 | 3-Methyl-cyclohexyl |
| 24 | 2-n-propyl-phenyl |
| 25 | Benzyl |
| 26 | 1-Phenyl-ethyl |

EXAMPLE 7

Each of the brominated esters of Example 6 is converted to 4,6-dibromo-3-hydroxy-2-pyridinecarboxamide by reaction with ammonium hydroxide, as per Example 3 herein.

EXAMPLE 8

Each of the brominated esters of Example 6 is converted to a 3-acyloxy compound of the following formula, by reaction with an anhydride, $(R'CO)_2O$, in the presence of pyridine. The pyridine is stripped off in vacuo and the ester extracted from the residue with an organic solvent, such as benzene and chloroform. The product is recovered from the extract by crystallization.

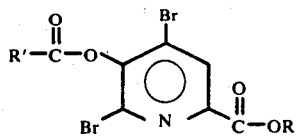

Illustrative of the "diesters" so produced are those of the preceding formula in which R' and R are as follows:

| Compound No. | R' | R |
|---|---|---|
| 27 | $CH_2=CH(CH_2)_7-CH_2-$ | $-CH_2-CH(CH_3)-CH_3$ |
| 28 | " | $-CH(CH_3)-(CH_2)_5CH_3$ |
| 29 | " | $-CH_2-C_6H_5$ |
| 30 | " | cyclopentyl |
| 31 | $CH_3-(CH_2)_9-CH_2-$ | cyclohexyl |
| 32 | " | $-C(CH_3)_2H$ |
| 33 | " | cycloheptyl |
| 34 | $C_6H_5-$ | $-CH(CH_3)-C_6H_5$ |
| 35 | " | 4-methyl-cyclohexyl |
| 36 | " | $-CH(CH_2CH_3)-C_6H_5$ (H) |
| 37 | $CH_3-CH(CH_3)-$ | $-CH(CH_3)-CH_3$ |
| 38 | " | $-CH_3$ |

EXAMPLE 9

Each of the diesters of Example 8 herein is saponified with one equivalent of a base, such as 5% aqueous NaOH, to form a sodium carboxylate salt of the formula

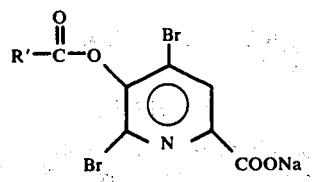

and the corresponding 2-pyridine acid

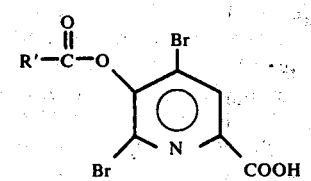

is then liberated by neutralization with a dilute mineral acid.

Illustrative of the 4,6-dibromo-3-acyloxy-2-pyridine carboxylic acids so produced are those derived from compounds 14 through 25 in the preceding example:

| Compounds of Example 8 Saponified | Acid Produced Compound No | R' |
|---|---|---|
| 27 through 30 | 39 | $CH_2=CH-(CH_2)_7-CH_2-$ |
| 31 - 33 | 40 | $CH_3(CH_2)_9-CH_2-$ |
| 34 - 36 | 41 | $C_6H_5-$ |

-continued

| Compounds of Example 8 Saponified | Acid Produced | |
|---|---|---|
| | Compound No | R' |
| 37, 38 | 42 | 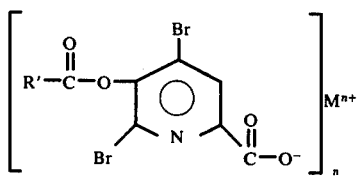 |

EXAMPLE 10

Metal carboxylate salts of the formula $$\left[ R'-\overset{O}{\underset{\|}{C}}-O-\underset{Br}{\overset{Br}{\bigcirc_N}}-\underset{C-O^-}{\overset{O}{\|}} \right]_n M^{n+}$$

are prepared by contacting dilute aqueous solutions of the sodium salts (see Example 9) with a cation exchange resin pre-loaded with ions of the metals listed in the summary description of the present invention. The following compounds are illustrative of said salts.

| Compound No. | R' | $M^{n+}$ |
|---|---|---|
| 43 | cyclohexenyl | $Mg^{2+}$ |
| 44 | $CH_3-\underset{\underset{CH_3}{\|}}{CH}-(CH_2)_2-CH_2-$ | $Cu^+$ |
| 45 | 2,3-dimethylphenyl | $Zn^{2+}$ |
| 46 | $C_6H_5-\underset{\underset{H}{\|}}{C}=CH-$ | $Fe^{3+}$ |
| 47 | $CH_3-CH_2-$ | $Sn^{2+}$ |
| 48 | phenyl | $Al^{3+}$ |

EXAMPLE 11

A. In the manner of Example 10, salts of the formula

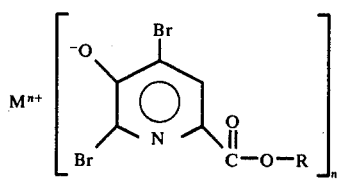

are prepared from the corresponding 3-hydroxy compounds (see Example 6). Illustrative of the salts so made are the following.

| Compound No. | R | $M^{n+}$ |
|---|---|---|
| 49 | $CH_3-$ | $K^+$ |
| 50 | $(CH_3)_2CH-\underset{\underset{CH_3}{\|}}{CH}-$ | $Ni^{2+}$ |
| 51 | cyclohexyl | $Mn^{2+}$ |
| 52 | $C_6H_5-CH_2-CH_2-$ | $Ba^{2+}$ |

B. 4,6-Dibromo-5-hydroxy-2-pyridine carboxylic acid is reacted with two equivalents of sodium hydroxide to produce the disodium salt. The latter in turn is converted, in the manner of Example 10, to double metal salts of the formula:

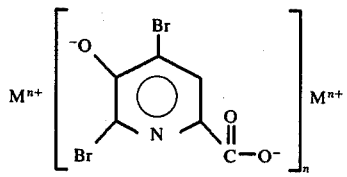

wherein $M^{n+}$ is a metal cation as defined in the summary of the invention herein and as exemplified in Example 10 and in part A of this example.

EXAMPLE 12

A. Ammonium salts of the formula

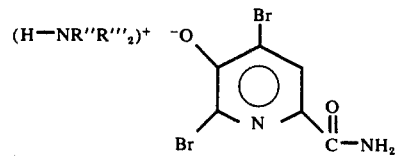

are prepared by adding an equivalent amount (or slight excess thereover) of ammonia (as aqueous ammonia) or of an amine, a morpholine or a piperidine, to a stirring aqueous dispersion of 4,6-dibromo-3-hydroxy-2-pyridine carboxamide. Illustrative of salts so prepared are those derived from the following NR''R$_2$''' compounds:

| Compound No. | NR''R$_2$''' |
|---|---|
| 53 | Ammonia |
| 54 | n-Butylamine |
| 55 | Diethylamine |
| 56 | Diallylamine |
| 57 | Methylisopropylamine |
| 58 | Ethanolamine |
| 59 | Triethanolamine |
| 60 | Diethylisopropyl amine |

-continued

| Compound No. | NR''R₂''' |
|---|---|
| 61 | Mixed branched-chain amines of formula $C_{22}H_{45}NH_2$ |
| 62 | Laurylamine |
| 63 | 3 Dimethylamino-1-butanol |
| 64 | Allyldimethylamine |
| 65 | 1-Diethylamino-5-hexanol |
| 66 | Cyclopropylamine |
| 67 | 3-Methyl-1-aminocyclohexane |
| 68 | Cycloheptylamine |
| 69 | Benzylamine |
| 70 | Morpholine |
| 71 | Piperidine |
| 72 | N-methylmorpholine |
| 73 | 1-Dodecylpiperidine |
| 74 | n-Propylamine |
| 75 | Triisopropanolamine |

B. The sodium and potassium salts (compounds 76 and 77 respectively) of 4,6-dibromo-5-hydroxy-2--pyridinecarboxamide are made by stirring the latter compound in aqueous solutions of the corresponding bases, NaOH and KOH. Either salt is then employed, in the manner of Example 10, to prepare metal salts of the formula

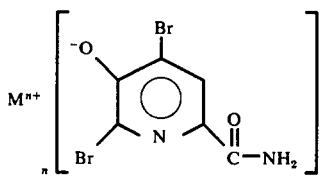

wherein $M^{n+}$ is each of the ions illustrated in Examples 10 and 11.

EXAMPLE 13

A. In the manner of Example 12, "ammonium" salts of the carboxyl group in each of compounds 39 through 42 (Example 9) are prepared with each of the NR''R₂''' compounds listed in Example 12.

B. In the manner of Example 12, two or slightly more than two equivalents of each of the NR''R₂''' compounds listed therein are reacted with 4,6-dibromo-5-hydroxy-2--pyridine carboxylic acid to form corresponding double salts of the formula:

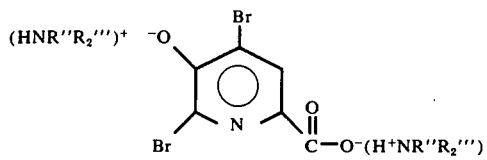

How the Compounds are Used

The compounds of the present invention are not limited to application as selective herbicides. They are also suitable for more general herbicidal use. The compounds have generally not been found as highly effective as pre-emergent herbicides, but may be so employed with good results against some plant species. Certain of the compounds also have insecticidal and/or fungicidal activity.

The practice of the present invention in any of its numerous embodiments can in some instances be carried out with unmodified compound; however, for good results, it is generally necessary that the compound be employed in modified form, that is, as one component of a composition formulated to implement the plant growth-inhibiting effects. Thus, for example, the active agent can be mixed with water or other liquid or liquids, preferably aided by the usage of a surface active agent. The active agent can also be incorporated on a finely divided solid, which can be a surface active substance, to yield a wettable powder, which can subsequently be dispersed in water or other liquid, or incorporated as part of a dust which can be applied directly. Other methods of formulations are known in the art and can be employed in implementing the present invention.

In carrying out the novel method of the present invention, the exact amount of the active agent employed is not critical and will vary, depending upon the type of growth-inhibiting effect desired, the identity of the plants concerned, the particular active agent used, weather conditions, and the like. In general, a broad growth-inhibiting effect is obtained with rates of from 3–5 to 20 pounds or more of active agent per acre, and such rates are suitable and effective for control of vegetative growth on fallow land. When it is desired to obtain a selective growth-inhibiting effect on weeds in areas containing crop plants such as wheat and barley, rates of from 0.25 or less to 5 pounds generally give good results. When in the typical mode of operation, the active agent is employed as a composition comprising the agent, the exact concentration of active agent in the composition is not critical, except that the concentration and total amount of formulation employed be adequate to supply the appropriate amount of active agent on a per acre basis. In general, good results are obtained when employing formulations containing the active agent in a concentration of from 0.5 to 10 percent or higher, in the instance of a liquid formulation; and in a concentration of from 1.0 to 5.0 percent or higher, in the instance of a dust, powder, granule, or the like. More concentrated formulations can be prepared and are often preferred in that they can serve, depending upon the particular application contemplated and the particular concentration, both as a concentrated formulation for purposes of shipment, storage, and the like, and as an ultimate treating composition. Thus, for example, formulations often preferably contain a surface active agent and the present active agent, the latter being present in an amount of from 0.5 to 99.5 percent, by weight; or an inert, finely divided solid and the present active agent, the latter being present in an amount of from 1.0 to 99.0 percent, by weight. Such formulations, as indicated, can be employed directly in certain applications, but can also be diluted and subsequently employed in many other applications.

Liquid compositions containing the desired amount of active agent are prepared by dissolving the substance in a liquid with or without the aid of a surface active dispersing agent such as an ionic or non-ionic emulsifying agent. Most preferably, the subject compound is dissolved in water or in an organic liquid carrier, aided by the use of a surface active dispersing agent. Suitable such organic liquid carriers include agricultural spray oils and the petroleum distillates such as diesel fuel, kerosene, fuel oil naphthas and Stoddard solvent. The choice of dispersing and emulsifying agents and the amount thereof employed is dictated by the nature of the composition and by the ability of the agent to facilitate the dispersion of the active agent in the carrier to produce the desired composition. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, and the like. Representative surface active agents which are suitably employed in implementing the present invention are identified in U.S. Pat. Nos. 3,095,299, second column, lines 25-36; 2,655,447, column 5, and 2,412,510, columns 4 and 5.

In the preparation of dust compositions, the active ingredient is intimately dispersed in and on a finely divided solid such as clay, talc, chalk, gypsum, limestone, vermiculite fines, perlite, and the like. In one method of achieving such dispersion, the finely divided carrier is mechanically mixed or ground with the active agent.

Similarly, dust compositions containing the toxicant compounds can be prepared with various of the solid surface active dispersing agents such as bentonite, fuller's earth, attapulgite and other clays. Depending upon the proportions of ingredients, these dust compositions can be employed as concentrates and subsequently diluted with additional solid surface active dispersing agents or with chalk, talc, or gypsum and the like to obtain the desired amount of active ingredient in a composition adapted to be employed for the suppression of the growth of the plants. Also, such dust compositions can be dispersed in water, with or without the aid of a dispersing agent, to form spray mixtures.

Formulations containing the present active agent are often advantageously further modified by incorporation therein of an effective amount of a surfactant which facilitates the dispersion and spreading of the formulation of the plant leaf surfaces and the incorporation of the formulation by the plant.

In accordance with the present invention, the active agent can be dispersed in soil or other growth media in any convenient fashion. Applications can be carried out by simply mixing with the media, by applying to the surface of soil and thereafter dragging or discing into the soil to the desired depth, or by employing a liquid carrier to accomplish the penetration and impregnation. The application of spray and dust compositions to the surface of soil, or to plant parts or the above ground surfaces of plants can be carried out by conventional methods, e.g., power dusters, boom and hand sprayers and spray dusters, whether surface or air-borne. However, while such conventional modes of application can be used, they are not required. As above noted, it is an advantage of the present invention that the compounds serving as active agent are active and effective as herbicides when merely placed on the surface of the soil, without any additional step to assist incorporation. Thus, the compounds are of substantially the same efficacy regardless of whether they are applied to the surface only, or wheter they are applied to the surface and subsequently disced into the soil.

In a further method, the distribution of the active agent in soil can be accomplished by introducing the agent into the water employed to irrigate the soil. In such procedures, the amount of water is varied with the porosity and water holding capacity of the soil to obtain a desired depth of distribution of the agent.

In addition, the present method also comprehends the employment of an aerosol composition containing one or more of the present active agents as an active compound. Such a composition is prepared according to conventional methods wherein the agent is dispersed in a solvent, and the resultant dispersion mixed with a propellant in liquid state. Such variables as the particular agent to be used and the nature of the vegetation which is to be treated will determine the desirability of the solvent and concentration of the agent therein.

Satisfactory results are obtained when the active agent of the present invention, or a composition comprising such active agent, is combined with other agricultural materials intended to be applied to plants, plant parts, or their habitats. Such materials include fertilizers, fungicides, nematocides, insecticides, other herbicides, soil conditioning agents, and the like.

The following further examples illustrate the general herbicidal utility of the compounds of the present invention.

EXAMPLE 14

Compounds representative of the genus disclosed herein were tested as post-emergent herbicides by the following procedure.

Pots are filled with a sandy soil, and plants of any species considered appropriate (such as pigweed, field bindweed, velvetleaf, cotton, barnyard grass, foxtail, wild oat, and crabgrass) are grown to an average height of 2 to 4 inches. Plants are then sprayed to run-off with an aqueous solution of dispersion containing the test chemical at the desired concentration. The plants are maintained in the greenhouse and are sub-irrigated as necessary. Final readings are made 2 weeks after treatment. Readings represent the percent kill or control of growth on the treated plants when compared to untreated plants, with 0 = no visible effects and 100 = all plants dead. Observations are also made on the type of injury such as burn, chlorosis and stunting. Code designations for various plant responses are as follows:

1 = Burn; 2 = chlorosis; 7 = stunt, retarded growth.

Compounds found active are subsequently tested over a range of rates which are less than the initial rate. The procedure is the same as described above except that additional species (such as soybean, corn, wheat, ragweed, Johnson grass, etc.) are used. Additionally, test chemicals may be applied to the soil surface by drenching or as a solid to preclude contact with foliage. If foliage is sprayed, the pots are subsequently maintained by sub-irrigation; if chemical application is made to the soil, the pots are topwatered.

TABLE I

Post-emergent Herbicide Test Results
Compound Structure and Number[1]

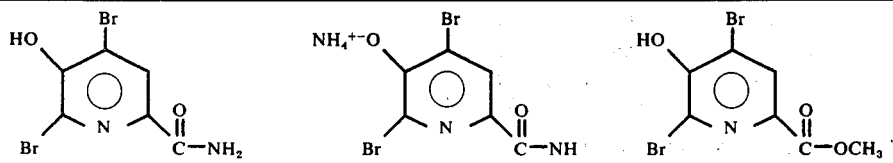

| | (3) | | | (53) | | | (2) | | |
|---|---|---|---|---|---|---|---|---|---|
| Plant Species | Conc'n[2] | % Control | Symp.[3] | Conc'n | % Control | Symp. | Conc. | % Control | Symp. |
| Pig weeds | 500 | 100 | 1,7 | 1000 | 100 | 1 | 4000 | 85 | 1,7 |
| Soybean | 4000 | 90 | 1,7 | 4000 | 75 | 1 | 500 | 0 | — |
| Cotton | 500 | 95 | 1,7 | 2000 | 100 | 1 | 4000 | 0 | — |
| German Millet | 2000 | 90 | 1,7 | 2000 | 100 | 1 | 4000 | 40 | 1,7 |
| White winter Wheat | 4000 | 0 | — | 4000 | 20 | 7 | 4000 | 0 | — |
| Crabgrass | 4000 | 90 | 1,7 | 4000 | 30 | 1,7 | 4000 | 0 | — |
| Corn | 4000 | 20 | 1,2,7 | 4000 | 70 | 2,7 | 4000 | 0 | — |
| Bindweed | 4000 | 25 | 1,7 | 4000 | 60 | 1,7 | 4000 | 0 | — |
| Johnson Grass | 4000 | 90 | 1,7 | 4000 | 25 | 1,7 | 4000 | 0 | — |
| Barnyard Grass | 4000 | 95 | 1,7 | 4000 | 95 | 1 | 4000 | 0 | — |
| Wild Oats | 2000 | 90 | 1,7 | 2000 | 95 | 1 | 4000 | 15 | 1,7 |
| Rape | 500 | 100 | 1,7 | 1000 | 100 | 1 | 4000 | 25 | 1,7 |
| Cultured Rice | 4000 | 60 | 1,7 | 4000 | 20 | 1,2,7 | 4000 | 0 | — |
| Velvetleaf | 125 | 95 | 1,7 | 250 | 100 | 1 | 4000 | 0 | — |
| Morning Glory | 500 | 70 | 1,7 | — | — | — | 4000 | 0 | — |
| Sorghum/Milo | 4000 | 10 | 1,7 | 4000 | 60 | 1,7 | 4000 | 0 | — |
| Beans | — | — | — | 4000 | 85 | 2,7 | 4000 | 40 | 7 |
| Yellow Foxtail | 4000 | 0 | — | 4000 | 80 | 1,2,7 | 4000 | 0 | — |
| Wild Mustard | — | — | — | — | — | — | 4000 | 45 | 1 |

Note:
[1] See preparative examples 3, 12 and 2, respectively
[2] Parts per million
[3] Injury symptoms

EXAMPLE 15

The representative compounds of the preceding example were also tested as pre-emergent herbicides, using the following procedure.

Pots are filled to within 1 inch of the top with a medium-textured soil and seeds of any species considered appropriate (such as pig weed, field bindweed, velvetleaf, cotton, barnyard grass, foxtail, wild oat and crabgrass) are sown in thier appropriate area. The seeds are then covered with a ½-inch layer of a sandy soil and test chemicals formulated at the desired concentration are drenched onto the soil surface in sufficient volume to wet the top 1½ to 2 inches of soil. The pots are maintained in the greenhouse and are top-watered as necessary. Final readings are made about 2 weeks after treatment, the exact time depending upon the rate of plant growth. Readings are based on the germination and the growth of treated plants compared with that of untreated plants. Readings of 0 percent = no visible effects and 100 percent = all plants dead. Observations are also made on the type of injury such as burn, chlorosis, and stunting. Number designations for various plant responses are given below.

Evaluation - Compounds found active are subsequently tested over a range of rates which are less than the initial rate. The procedure is the same as described above with the exceptions that the seeds of appropriate species (such as soybean, corn, wheat, ragweed, Johnson grass, ect.) are covered with the same medium-textured soil used to fill the pot, and the chemicals are sprayed onto the soil surface at the desired rate in sufficient volume to cover and wet the soil surface. The pots are maintained, top-watered, and graded as described above.

Injury Designations:
| | |
|---|---|
| 1 = Burn | 6 = Epinasty, stem curl |
| 2 = Chlorosis | 7 = Stunt, retarded growth |
| 3 = Malformed leaves | 8 = Stimulated growth |
| 4 = Stand reduction | 9 = Regrowth |
| 5 = Defoliation | 0 = Grew then died |

TABLE II

Pre-emergent Herbicide Test Results

| Compound No. | (3)[1] | | | (53)[1] | | | (2)[1] | | | (12)[2] | | (13)[3] | |
|---|---|---|---|---|---|---|---|---|---|---|---|---|---|
| Plant Species | Rate[4] | Control[5] | Symp.[6] | Rate | Control | Symp. | Rate | Control | Symp. | Rate | Control | Rate | Control |
| Pig Weeds | 10 | 30 | 2,7 | 10 | 100 | 0 | 20 | 90 | 7 | 10 | 90 | 10 | — |
| Cotton | " | 45 | 2,7 | " | 100 | 0 | — | — | — | " | 100 | " | — |
| Crabgrass | " | 0 | — | " | 20 | 2,7 | 20 | 0 | — | " | 40 | " | 100 |
| Bindweed | " | 40 | — | 4 | 25 | 7 | " | 50 | 7 | — | — | — | — |
| Barnyard Grass | " | 60 | 7 | 10 | 80 | 2,7 | " | 0 | — | 10 | 80 | 10 | 100 |
| Wild Oats | " | 100 | 0 | 4 | 95 | 0 | " | 0 | — | " | 80 | " | 100 |
| Yellow Foxtail | " | 55 | 2,7 | 10 | 40 | 2,7 | " | 0 | — | " | 80 | " | 100 |
| Velvet Leaf | " | 40 | 2,7 | " | 35 | 2,7 | " | — | — | " | 0 | " | 95 |
| Sorghum/mild | " | 30 | 2,7 | 10 | 45 | 7 | " | — | — | — | — | — | — |
| Beans | " | 25 | 2,7 | " | 25 | 7 | " | 30 | 7 | — | — | — | — |
| Soybeans | — | — | — | 4 | 0 | — | " | — | — | — | — | — | — |
| German Millet | — | — | — | 4 | 40 | 1,7 | — | — | — | — | — | — | — |
| White Winter Wheat | — | — | — | " | 0 | — | — | — | — | — | — | — | — |
| Corn | — | — | — | 4 | 15 | 7 | — | — | — | — | — | — | — |
| Johnson Grass | — | — | — | " | 15 | 7 | — | — | — | — | — | — | — |
| Rape | — | — | — | " | 0 | — | — | — | — | — | — | — | — |

TABLE II-continued

| Compound No. Plant Species | (3)[1] | | | (53)[1] | | | (2)[1] | | | (12)[2] | | (13)[3] | |
|---|---|---|---|---|---|---|---|---|---|---|---|---|---|
| | Rate[4] | Control[5] | Symp.[6] | Rate | Control | Symp. | Rate | Control | Symp. | Rate | Control | Rate | Control |
| Cultured Rice | — | — | — | ″ | 10 | 1,7 | — | — | — | — | — | — | — |
| Morning Glory | — | — | — | ″ | 0 | — | — | — | — | 10 | 80 | 10 | 50 |
| Wild Mustard | — | — | — | ″ | — | — | 20 | 50 | 7 | — | — | — | — |

Note:
[1]See Table I.
[2](See Example 5) Benzoic acid ester of 4,6-dibromo-5-hydroxy-2-pyridine carboxamide.
[3](See Example 5) Isobutyric acid ester of 4,6-dibromo-5-hydroxy-2-pyridine carboxamide.
[4]Lbs/acre
[5]Percent control
[6]Injury symptoms

EXAMPLE 16

Compound 3 (see Table I, Example 14) was compared as a postemergent herbicide against standards (CARBYNE® and BROMINIL®) in greenhouse test. All of the plants used in the tests—which were carried out essentially by the procedure of Example 14—were robust plants grown in the greenhouse and were sprayed with the test formulations when they attained 1-2 inches in height. A high total spray volume (300 gallons per acre) and a surfactant (0.2 percent Tween 20®) were employed to ensure good wetting of the wild oat plants included in the test. The results, given in Table III, show compound 3 to be less effective than BROMINIL® for control of morning glory, smartweed and tartary buckwheat at concentrations of 125 ppm or less and much less effective than CARBYNE® in control of blackgrass.

However, the new compound is outstandingly superior for control of wild oats and definitely better for control of wild mustard, at levels nontoxic to wheat.

TABLE III

ACTIVITY-SELECTIVITY COMPARISONS
OF 4,6-DIBROMO-5-HYDROXY-2-PYRIDINE CARBOXAMIDE
WITH TWO STANDARDS PRESENTLY USED IN WHEAT

Plant Species — Percent Control

| Compound | Conc. in ppm | Wheat | Barley | Tame Oats | Wild Oats | Black-grass | Cheat-grass | Fall-panicum | Smart-weed | Morning Glory | Wild Mustard | Tartary Buckwheat |
|---|---|---|---|---|---|---|---|---|---|---|---|---|
| (3) | 4M[1] | 10 | 30 | 100 | 100 | 0 | 0 | 0 | 100 | 50 | 95 | 100 |
| | 2M | 0 | 0 | 90 | 90 | 0 | 0 | 0 | 100 | 40 | 95 | 100 |
| | 1M | 0 | 0 | 80 | 90 | 0 | 0 | 0 | 100 | 20 | 95 | 100 |
| | 500 | 0 | 0 | 80 | 80 | 0 | 0 | 0 | 100 | 0 | 85 | 100 |
| | 250 | 0 | 0 | 60 | 50 | 0 | 0 | 0 | 100 | 0 | 80 | 100 |
| | 125 | 0 | 0 | 50 | 40 | 0 | 0 | 0 | 70 | 0 | 70 | 90 |
| | 62 | 0 | 0 | 0 | 20 | 0 | 0 | 0 | 50 | 0 | 50 | 75 |
| | 31 | 0 | 0 | 0 | 20 | 0 | 0 | 0 | 30 | 0 | 0 | 50 |
| | 16 | 0 | 0 | 0 | 0 | 0 | 0 | 0 | 30 | 0 | 0 | 60 |
| BROMINIL® | 4M | 0 | — | — | 15 | — | — | — | 100 | 100 | 100 | 100 |
| | 2M | 0 | — | — | 0 | — | — | — | 100 | 100 | 100 | 100 |
| | 1M | 0 | 20 | — | 0 | — | — | — | 100 | 100 | 100 | 100 |
| | 500 | 0 | 10 | — | 0 | — | — | — | 100 | 90 | 100 | 100 |
| | 250 | 0 | 0 | — | 0 | — | — | — | 100 | 70 | 100 | 100 |
| | 125 | 0 | 0 | — | 0 | — | — | — | 100 | 40 | 100 | 100 |
| | 62 | 0 | 0 | — | 0 | — | — | — | 100 | 25 | 100 | 100 |
| | 31 | 0 | 0 | — | 0 | — | — | — | 95 | 0 | 95 | 85 |
| | 16 | 0 | 0 | — | 0 | — | — | — | 85 | 0 | 80 | 85 |
| CARBYNE® | 4M | 0 | — | — | 60 | 90 | 0 | 0 | — | — | 90 | — |
| | 2M | 0 | — | — | 70 | 90 | 0 | 0 | — | — | 60 | — |
| | 1M | 0 | — | — | 60 | 80 | 0 | 0 | — | — | 20 | — |
| | 500 | 0 | — | — | 15 | 60 | 0 | 0 | — | — | 0 | — |
| | 250 | 0 | — | — | 0 | 40 | 0 | 0 | — | — | 0 | — |
| | 125 | 0 | — | — | 0 | 0 | 0 | 0 | — | — | 0 | — |
| | 62 | 0 | — | — | 0 | 0 | 0 | 0 | — | — | 0 | — |
| | 31 | 0 | — | — | 0 | 0 | 0 | 0 | — | — | 0 | — |
| | 16 | 0 | — | — | 0 | 0 | 0 | 0 | — | — | 0 | — |

Note:
[1]M = 1000

EXAMPLE 17

In the manner of Example 16, tests were run with compound 3, formulated as a wettable powder, and with six different amine salts (see Example 12) of compound 3, as solutions in water. The wettable powder formulation consisted of the active agent, 2.25 parts by weight; Westvaco system 211–122 dispersant[1], 0.55 parts; Bentonite 0.025 parts and water, 2.17 parts. (The Westvaco dispersant used is a combination of a sodium lignosulfonate and a non-ionic wetting agent, in propylene glycol).

TABLE IV

ACTIVITY-SELECTIVITY COMPARISONS OF 4,6-DIBROMO-5-HYDROXY-2-PYRIDINE CARBOXAMIDE AND VARIOUS AMINE SALTS THEREOF

All compounds applied in total spray volume 300 gallons per acre. Surfactant 0.2% Tween-20[c]

Amine in salt and compound number[b]
Percent Control

| Species | Rate, ppm | diethyl-amine (55) | n-Butyl-amine (54) | Ethanol-amine (58) | Tri-isopropanol amine (75) | Triethanol-amine (59) | n-Propyl amine (74) | Wettable Powder |
|---|---|---|---|---|---|---|---|---|
| Wild Oats | 4M[a] | 100 | 100 | 100 | 100 | 100 | 100 | 95 |
| | 2M | 100 | 90 | 95 | 98 | 98 | 98 | 95 |
| | 1M | 85 | 80 | 95 | 95 | 98 | 98 | 95 |
| | 500 | 75 | 70 | 85 | 80 | 90 | 90 | 90 |
| | 250 | 75 | 50 | 60 | 60 | 70 | 50 | 50 |
| | 125 | 50 | 30 | 40 | 40 | 60 | 50 | 20 |
| Wheat | 4M | 50 | 85 | 85 | 50 | 85 | 90 | 10 |
| | 2M | 30 | 60 | 60 | 50 | 60 | 50 | 0 |
| | 1M | 20 | 10 | 40 | 20 | 40 | 20 | 0 |
| | 500 | 0 | 0 | 0 | 20 | 0 | 0 | 0 |
| | 250 | 0 | 0 | 0 | 0 | 0 | 0 | 0 |

Notes:
[a] M = 1000
[b] See Example 12
[c] A polyoxyethylene derivative of a fatty acid partial ester of a sorbitan.

EXAMPLE 18

Six representative carboxylate esters of 4,6-dibromo-5-hydroxy-2-pyridinecarboxamide were tested as post-emergent herbicides, at a concentration of 4000 ppm, in the manner of Example 14. These compounds were also tested as pre-emergent herbicides in the manner of Example 15. The results are given in Tables V and VI, respectively.

EXAMPLE 19

Three of the more active esters of Example 18 and the sodium salt of 4,6-dibromo-5-hydroxy-2-pyridine carboxamide were formulated in a solution of 1 parts by weight of dimethyl formamide, 2 parts of acetone and 3 parts of water containing 0.2 percent TWEEN-20® surfactant. These formulations were compared to the wettable powder formulation (Example 17) of 4,6-

TABLE V

POST-EMERGENCE HERBICIDE TEST RESULTS

Ester and Compound Number[1]
% Control at 4000 ppm

| Plant Species | Acetate (6) | Propanoate (7) | N-Butyrate (8) | n-Hexanoate (9) | n-Octanoate (5) | n-Dodecanoate (11) |
|---|---|---|---|---|---|---|
| Sorghum | 65 | 15 | 10 | 40 | 0 | 0 |
| Wild Oats | 80 | 75 | 35 | 100 | 80 | 45 |
| Foxtail | 50 | 45 | 50 | 35 | 25 | 0 |
| Barnyard Grass | 65 | 45 | 45 | 65 | 10 | 15 |
| Crab grass | 45 | 0 | 0 | 75 | 0 | 0 |
| Bean | 35 | 30 | 15 | 30 | 0 | 0 |
| Cotton | 100 | 95 | 25 | 70 | 85 | 0 |
| Pigweed | 85 | 100 | 100 | 100 | 40 | 0 |
| Bindweed | 30 | 35 | 0 | 55 | 20 | 0 |
| Velvet Leaf | 95 | 75 | 55 | 70 | 35 | 0 |

Note:
[1] See Example 5.

TABLE VI

PRE-EMERGENCE HERBICIDE TEST RESULTS

Ester and Compound Number[1]
Application Rate; Lbs/Acre / % Control

| Plant Species | Acetate (6) | | Propanoate (7) | | n-Butyrate (8) | | n-Hexanoate (9) | | n-Octanoate (5) | | n-Dodecanoate (11) |
|---|---|---|---|---|---|---|---|---|---|---|---|
| Corn | 4 | | 25 | — | — | — | — | — | — | — | — |
| Rice | | | 0 | — | — | — | — | — | — | — | — |
| Wheat | | | 0 | — | — | — | — | — | — | — | — |
| Sorghum | | | 0 | 10 | 60 | 10 | 35 | 10 | 60 | 10 | 55 | 10 | 50 |
| Wild Oats | | | 90 | | 50 | | 90 | | 100 | | 85 | | 70 |
| Foxtail | | | 70 | | 95 | | 100 | | 95 | | 90 | | 80 |
| Barnyard Grass | 10 | | 95 | | 85 | | 95 | | 90 | | 90 | | 35 |
| Crab grass | | | 90 | | 70 | | 100 | | 75 | | 100 | | 100 |
| Johnson Grass | 4 | | 0 | — | — | — | — | — | — | — | — |
| Rape | | | 35 | — | — | — | — | — | — | — | — |
| Bean | 10 | | 65 | | 25 | | 85 | | 45 | | 60 | | 45 |
| Cotton | | | 95 | | 30 | | 95 | | 100 | | 0 | | 0 |
| Pigweed | 2 | | 100 | | 80 | | 85 | | 75 | | 90 | | 80 |
| Bindweed | 10 | | 70 | | 50 | | 45 | | 80 | | 50 | | 0 |
| Velvet Leaf | | | 85 | | 80 | | 80 | | 100 | | 80 | | 60 |

Note:
[1] See Example 5.

dibromo-5-hydroxy-2-pyridine carboxamide as post-emergent herbicides, in the manner of Example 16, but at a total spray volume of only 150 gallons per acre. The results are given in Table VII.

X-77® was used, at a 0.2 percent level, to enhance wetting. The total spray volume was 20 gallons per acre.

TABLE VII

POST-EMERGENT HERBICIDE COMPARISON Percent Control On

| Compound and Number[1] | Conc'n ppm | Wheat | Barley | Wild Oats | Wild Mustard | Jimson Weed | Buckwheat | Morning Glory |
|---|---|---|---|---|---|---|---|---|
| Esters | | | | | | | | |
| Acetate | 4000 | 10 | 10 | 90 | 100 | 100 | 100 | 50 |
| (6) | 500 | 0 | 0 | 90 | 90 | 100 | 90 | 0 |
| Propanoate | 4000 | 10 | 10 | 100 | 100 | 100 | 100 | 20 |
| (7) | 250 | 10 | 10 | 95 | 70 | 100 | 50 | 0 |
| Octanoate | 4000 | 0 | 0 | 90 | 90 | 100 | 30 | 20 |
| (5) | 500 | 0 | 0 | 90 | 50 | 100 | 10 | 0 |
| Na-salt | 2000 | 10 | 10 | 100 | 100 | 100 | 100 | 70 |
| (76) | 500 | 0 | 0 | 30 | 50 | 100 | 70 | 0 |
| Wettable | 2000 | 10 | 10 | 95 | 100 | 100 | 90 | 20 |
| Powder | 1000 | 0 | 0 | 85 | 90 | 100 | 90 | 0 |
| (3) [structure: 3,4-dibromo-5-hydroxypyridine-2-carboxamide] | 500 | 0 | 0 | 70 | 70 | 90 | 70 | 0 |

Note:
[1] See preparative Examples 3, 5 and 12(B).

EXAMPLE 20

Representative compounds of the invention, having the following formula, were tested as post-emergent herbicides on two varieties of wheat, wild mustard, green foxtail and wild oats - the latter at each of three different stages of growth. COLLOIDAL TRITON

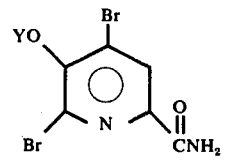

TABLE VIII

POST-EMERGENT HERBICIDE TESTS AT LOW RATES OF APPLICATION

| Y in YO-[structure]-CNH$_2$ and Compound Number[1] | Rate Lbs/Acre | Wheat Chris | Wheat Bounty | Wild Oats 4 wks old | Wild Oats 3 wks old | Wild Oats 2 wks old | Wild Mustard | Gr Foxtail |
|---|---|---|---|---|---|---|---|---|
| Na$^+$ (76) | 1 | 0 | 0 | 0 | 0 | 0 | 0 | 0 |
| $[HN(CHCH_2OH\,|\,CH_3)_3]^+$ (75) | 1 | 0 | 0 | 30 | 50 | 10 | 90 | 50 |
| $[HN(CH_2-CH_2OH)_3]^+$ (59) | 1 | 10 | 10 | 95 | 100 | 50 | 50 | 0 |
|  | ½ | 0 | 0 | 50 | 30 | 0 | 0 | 0 |
| $[H_2N(CH_2CH_3)_2]^+$ (55) | 1 | 0 | 0 | 0 | 0 | 0 | 50 | 0 |
| $[H_3N-CH_2-CH_2OH]^+$ (58) | 1 | 0 | 0 | 20 | 30 | 0 | 80 | 0 |
| H$^+$ | ½ | 0 | 0 | 80 | 10 | 0 | 80 | 0 |

TABLE VIII-continued
POST-EMERGENT HERBICIDE TESTS AT LOW RATES OF APPLICATION

| Y in YO-pyridine-CNH$_2$ structure (Br, Br substituents) and Compound Number[1] | Rate Lbs/Acre | Wheat Chris | Wheat Bounty | % Control On Wild Oats 4 wks old | 3 wks old | 2 wks old | Wild Mustard | Gr Foxtail |
|---|---|---|---|---|---|---|---|---|
| (3) Wettable Powder | 1 | 20 | 0 | 90 | 95 | 0 | 100 | 0 |
| 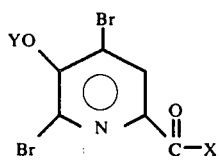 (72) | ½ | 10 | 0 | 30 | 10 | 0 | 95 | 0 |
| CH$_3$CO— (6) | 1 | 0 | 0 | 100 | 95 | 20 | 100 | 30 |
|  | ½ | 0 | 0 | 60 | 50 | 50 | 20 | 10 |

Note:
[1]See Table I.

I claim:

1. A compound of the formula

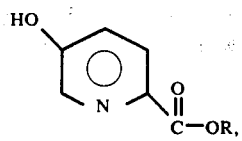

wherein X is -OR or -NH$_2$; Y is H, M or R'CO-; R is a primary or secondary C$_1$-C$_{12}$ alkyl group, a C$_5$-C$_7$ cycloalkyl group, phenyl or a C$_7$-C$_{12}$ phenalkyl or alkylphenyl group; R' is a C$_1$-C$_{12}$ alkyl or alkenyl group, a C$_5$-C$_7$ cycloalkyl or cycloalkenyl group, phenyl or a C$_7$-C$_{12}$ phenalkyl, phenalkenyl, alkylphenyl or alkenylphenyl group; and M is a metal or ammonium (HNR'λ'R$_2$''')$^+$cation, said metal being lithium, sodium, potassium, calcium, magnesium, barium, aluminum, a metal of atomic number 24 through 30 or tin and R'' is H, an alkyl or alkenyl group of 1 to 22 carbons, a hydroxyalkyl group of 2 to 4 carbons, a cycloalkyl group of 3 to 7 carbons or benzyl; and the two R''40 groups, together with the nitrogen, constitute a morpholine or piperidine ring or are independently defined as in R''.

2. A compound of claim 1 wherein X is —NH$_2$.

3. A compound of claim 2 wherein Y is H, Na$^+$, (HNR''R$_2$''')$^+$or R'CO and R' is a linear alkyl group of 1 to 11 carbons.

4. A compound of claim 3 wherein Y is H or R'CO and R' contains 1 to 7 carbons.

5. A compound of claim 3 wherein Y is (HNR''R$_2$''')$^+$.

6. A compound of claim 5 wherein Y is (H-N(CH$_2$-CH$_2$OH)$_3$)$^+$ or

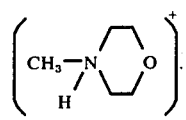

7. The compound of claim 2 which is 4,6-dibromo-5-hydroxy-2-pyridine carboxamide.

8. The compound of claim 3 which is 4,6-dibromo-5-acetyloxy-2-pyridine carboxamide.

9. The compound of claim 6 which is the triethanolamine salt of 4,6-dibromo-5-hydroxy-2-pyridine carboxamide.

10. The compound of claim 6 which is the N-methylmorpholine salt of 4,6-dibromo-5-hydroxy-2-pyridine carboxamide 11. A process for the preparation of 4,6-dibromo-5-hydroxy-2-pyridine carboxamide which comprises reacting an ester of the formula

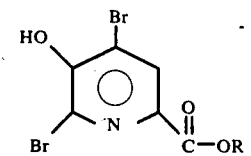

wherein R is defined as in claim 1, with bromine, by contacting a dispersion or solution of said ester in water with said bromine, to produce a 4,6-dibromo derivative of the formula and then reacting said dibromo derivative with aqueous ammonia, thereby converting the —COOR group to a —CONH$_2$ group.

12. The process of claim 11 wherein R is a primary or secondary alkyl group of 1 to 12 carbons.

13. The process of claim 11 wherein R is methyl or ethyl.

14. A method of controlling plant growth comprising distributing in an area where the plants are grown, in an amount effective to control their growth, a compound of claim 1.

15. The method of claim 14 wherein the compound is 4,6-dibromo-5-hydroxy-2-pyridine carboxamide or 4,6-dibromo-5-acetyloxy-2-pyridine carboxamide.

* * * * *

UNITED STATES PATENT AND TRADEMARK OFFICE
CERTIFICATE OF CORRECTION

PATENT NO. : 4,025,333

DATED : May 24, 1977

INVENTOR(S) : A. H. Gulbenk

It is certified that error appears in the above-identified patent and that said Letters Patent are hereby corrected as shown below:

Column 6, line 41, the Alkanoyl Group for Compound No. 12 should be -- ØCO- --;

Columns 15-16, Table I, change the "$\overset{O}{\underset{}{\overset{\|}{C}}}-NH$" portion of center formula to -- $\overset{O}{\underset{}{\overset{\|}{C}}}-NH_2$ -- ;

Columns 19-20, Table IV, second line of sub-heading, after the word Tween-20 "R" should be shown as -- ® -- and "Cl" after ® should be lower case c with a slash after, as -- c/ -- ;

Column 22, Table VIII, last notation to be shown in first column should read -- $H^+$ -- ;
(3)
Wettable Powder

UNITED STATES PATENT AND TRADEMARK OFFICE
CERTIFICATE OF CORRECTION

PATENT NO. : 4,025,333
DATED : May 24, 1977
INVENTOR(S) : A. H. Gulbenk

It is certified that error appears in the above-identified patent and that said Letters Patent are hereby corrected as shown below:

Column 23, line 42, after ammonium, line should read -- $(HNR''R_2''')^+$ -- continuing on line 43 with "cation" ;

Column 23, line 48, after the word "two" delete "R"40" and insert -- R''' -- .

Signed and Sealed this

*Fifteenth* Day of *November 1977*

[SEAL]

Attest:

RUTH C. MASON
*Attesting Officer*

LUTRELLE F. PARKER
*Acting Commissioner of Patents and Trademarks*